(12) United States Patent
Wang et al.

(10) Patent No.: US 9,730,657 B2
(45) Date of Patent: Aug. 15, 2017

(54) COMPUTED TOMOGRAPHY BASED ON LINEAR SCANNING

(71) Applicants: Ge Wang, Loudonville, NY (US); Fenglin Liu, Troy, NY (US); Wenxiang Cong, Albany, NY (US); Hengyong Yu, Winston-Salem, NC (US)

(72) Inventors: Ge Wang, Loudonville, NY (US); Fenglin Liu, Troy, NY (US); Wenxiang Cong, Albany, NY (US); Hengyong Yu, Winston-Salem, NC (US)

(73) Assignee: Rensselaer Polytechnic Institute, Troy, NY (US)

( * ) Notice: Subject to any disclaimer, the term of this patent is extended or adjusted under 35 U.S.C. 154(b) by 254 days.

(21) Appl. No.: 14/573,967

(22) Filed: Dec. 17, 2014

(65) Prior Publication Data

US 2015/0170361 A1    Jun. 18, 2015

Related U.S. Application Data

(60) Provisional application No. 61/916,834, filed on Dec. 17, 2013.

(51) Int. Cl.
| | |
|---|---|
| *A61B 6/03* | (2006.01) |
| *A61B 6/00* | (2006.01) |
| *A61B 6/02* | (2006.01) |
| *G06T 11/00* | (2006.01) |

(52) U.S. Cl.
CPC ............ *A61B 6/4007* (2013.01); *A61B 6/025* (2013.01); *A61B 6/027* (2013.01); *A61B 6/4014* (2013.01); *A61B 6/5205* (2013.01); *G06T 11/006* (2013.01); *A61B 6/032* (2013.01); *A61B 6/035* (2013.01); *A61B 6/4452* (2013.01); *G06T 2211/432* (2013.01); *G06T 2211/436* (2013.01)

(58) Field of Classification Search
CPC .. A61B 6/00; A61B 6/025; A61B 6/03; A61B 6/032; A61B 6/035; A61B 6/4007; A61B 6/4014; A61B 6/4452; A61B 6/5205; A61B 6/5211; A61B 6/4429; G06T 7/00; G06T 7/0012; G01N 23/046; G01N 23/08; G01N 23/083
USPC ................. 378/4, 9, 10, 11, 21, 25, 26, 901
See application file for complete search history.

(56) References Cited

U.S. PATENT DOCUMENTS

2008/0267484 A1* 10/2008 Chen ...................... A61B 6/032
382/132

OTHER PUBLICATIONS

Andersen, A.H. et al., "Simultaneous Algebraic Reconstruction Technique (SART): A Superior Implementation of the Art Algorithm," *Ultrasonic Imaging*, 1984, 6(1):81-94.
(Continued)

*Primary Examiner* — Jurie Yun
(74) *Attorney, Agent, or Firm* — Saliwanchik, Lloyd & Eisenschenk

(57) ABSTRACT

Imaging methods and imaging systems are provided. Methods and systems of the subject invention can include linearly translating a source and a detector. The source and the detector can be moved in opposite or approximately opposite directions. Acquired data can be used to reconstruct a tomographic image by using, for example, a compressive sensing technique.

20 Claims, 10 Drawing Sheets

(56) References Cited

OTHER PUBLICATIONS

Candes, Emmanuel et al., "Robust Uncertainty Principles: Exact Signal Reconstruction from Highly Incomplete Frequency Information," *IEEE Transactions on Information Theory*, 2006, 52(2):489-509.

Chen, Guang-Hong et al., "Prior image constrained compressed sensing (PICCS): A method to accurately reconstruct dynamic CT images from highly undersampled projection data sets," *Medical Physics*, 2008, 35(2):660-663.

Courdurier, M. et al., "Solving the Interior Problem of Computed Tomography Using a Priori Knowledge," *Inverse Problems*, 2008, 24(6):1-37.

Donoho, David L. "Compressed Sensing," *IEEE Transactions on Information Theory*, 2006, 52(4):1289-1306.

Feldkamp, L.A. et al., "Practical cone-beam algorithm," *Journal of the Optical Society of America: A*, 1984, 1(6):612-619.

Flohr, Thomas G. et al., "First performance evaluation of a dual-source CT (DSCT) system," *European Radiology*, 2006, 16(2):256-268.

Fuchs, Victor R. et al., "Physicians' Views of the Relative Importance of Thirty Medical Innovations," *Health Affairs*, 2001, 20(5):30-42.

Gordon, Richard et al., "Algebraic Reconstruction Techniques (ART) for Three-dimensional Electron Microscopy and X-ray Photography," *Journal of Theoretical Biology*, 1970, 29(3):471-481.

Jensen, Nikolaj K.G. et al., "Prediction and Reduction of Motion Artifacts in Free-Breathing Dynamic Contrast Enhanced CT Perfusion Imaging of Primary and Metastatic Intrahepatic Tumors," *Academic Radiology*, 2013, 20(4):414-422.

Jiang, Ming et al., "Convergence Studies on Iterative Algorithms for Image Reconstruction," *IEEE Transactions on Medical Imaging*, 2003, 22:569-579.

Kudo, Hiroyuki et al., "Tiny a priori knowledge solves the interior problem in computed tomography," *Physics in Medicine and Biology*, 2008, 53(9):2207-2231.

Sechopoulos, Ioannis. "A review of breast tomosynthesis. Part I. The image acquisition process," *Medical Physics*, 2013, 40(1):1-12.

Sechopoulos, Ioannis. "A review of breast tomosynthesis. Part II. Image reconstruction, processing and analysis, and advanced applications," *Medical Physics*, 2013, 40(1):1-17.

Tonna, Joseph E. et al., "Potentially Low Cost Solution to Extend Use of Early Generation Computed Tomography," *Western Journal of Emergency Medicine*, 2010, XI(5):463-469.

Wang, Ge et al., "Ordered-Subset Simultaneous Algebraic Reconstruction Techniques (OS-SART)," *Journal of X-Ray Science and Technology*, 2004, 12(3):169-177.

Wang, Ge et al., "The meaning of interior tomography," *Physics in Medicine and Biology*, 2013, 58(16):R161-R186.

Xu, Qiong et al., "Statistical Interior Tomography," *IEEE Transactions on Medical Imaging*, 2011, 30(5):1116-1128.

Yang, Jiansheng et al., "High Order Total Variation Minimization for Interior Tomography," *Inverse Problems*, 2010, 26(3):1-40.

Ye, Yangbo et al., "A General Local Reconstruction Approach Based on a Truncated Hilbert Transform," *International Journal of Biomedical Imaging*, 2007, Article ID 63634, p. 1-8.

Yu, Hengyong et al., "A soft-threshold filtering approach for reconstruction from a limited number of projections," *Physics in Medicine and Biology*, 2010, 55(13):3905-3916.

Yu, Hengyong et al., "Compressed Sensing Based Interior Tomography," *Physics in Medicine and Biology*, 2009, 54(9):2791-2805.

Yu, Hengyong et al., "Local ROI Reconstruction via Generalized FBP and BPF Algorithms along More Flexible Curves," *International Journal of Biomedical Imaging*, 2006, Article ID 14989, p. 1-7.

\* cited by examiner (a)

(b)

(c)

(d)

(a)

(b)

(c)

(d)

(a)

(b)

(c)

(d)

COMPUTED TOMOGRAPHY BASED ON LINEAR SCANNING

CROSS-REFERENCE TO A RELATED APPLICATION

The present application claims the benefit of U.S. Provisional Application Ser. No. 61/916,834, filed Dec. 17, 2013, which is incorporated by reference herein in its entirety, including any figures, tables, and drawings.

BACKGROUND OF INVENTION

Computed Tomography (CT) is an important tool in diagnostic imaging. It plays a key role in diagnosis and intervention. Many advanced CT systems use wide detector arrays, multiple sources, and/or very fast rotation speed, for important clinical applications (e.g., coronary artery and whole organ perfusion imaging). As a result, modern CT scanners are expensive and are typically used by major hospitals and clinics in developed countries. Due at least in part to the expense, there is limited to no accessibility of CT systems for patients in rural areas of developing countries, disaster scenes, and battlefields.

Over the past decades, CT systems or methods have been proposed assuming linear translation-based scanning. These include a linear scan-based dental CT approach, a translation-based CT data acquisition method for imaging of a cable channel inside the corner formed by two walls in a building, and a linear scan CT system with a wide fan-angle source, a large-area detector, and an advanced image reconstruction algorithm. None of these proposed systems use interior tomography or are capable of ultra-low-cost CT in the case of general dose-effective medical applications.

BRIEF SUMMARY

The subject invention provides novel and advantageous imaging methods and imaging systems, capable of overcoming the limitations of related art imaging methods and systems. Methods and systems of the subject invention can include the use of linear scanning with an energy source and a detector in order to provide ultra-low-cost Computed Tomography (CT) imaging. An image reconstruction technique can be used, for example, one or more reconstruction algorithm(s).

In an embodiment, an imaging method can include: positioning an X-ray source on a first side of a subject to be imaged and facing the subject; positioning a detector on a second side of the subject and facing the subject; linearly translating the X-ray source and the detector by simultaneously moving the X-ray source and the detector in opposite or approximately opposite directions while the X-ray source supplies X-rays and the detector acquires tomographic data of the subject; and reconstructing a Computed Tomography (CT) image based on the tomographic data.

In another embodiment, an imaging system can include: a main stage for a subject to be imaged; a first X-ray source positioned to face a subject being imaged and configured to linearly translate while providing X-rays; and a first detector positioned to face a subject being imaged and to face the first X-ray source, and configured to linearly translate while acquiring tomographic data of a subject being imaged. The imaging system can be configured such that the first X-ray source and the first detector simultaneously move in opposite or approximately opposite directions while the first X-ray source supplies X-rays and the first detector acquires tomographic data.

DETAILED DISCLOSURE

The subject invention provides novel and advantageous imaging methods and imaging systems, capable of overcoming the limitations of related art imaging methods and systems. Methods and systems of the subject invention can include the use of linear scanning with an energy source and a detector in order to provide ultra-low-cost Computed Tomography (CT) imaging. An image reconstruction technique can be used, for example, one or more reconstruction algorithm(s).

Systems and method of the subject invention can be produced and/or used at a very low cost. Such systems and methods are advantageous in any setting but are especially advantageous in developing countries, particularly in rural areas. A data acquisition system can target a region of interest (ROI) to acquire data, which can be limited and/or truncated data. The source and detector can be translated in opposite or approximately opposite directions. Systems and methods of the subject invention can advantageously be used for ROI reconstruction with one or more localized linear scans, or global reconstruction by combining multiple ROI reconstructions. A slip ring that is often used in related art systems can be replaced by a translation-based setup, and the instrumentation cost is reduced by a relaxation of the imaging speed requirement. Several different translational scanning modes can be used. A system can be configured for a horizontal patient position or a vertical patient position. In an embodiment, ultra-low-cost X-ray CT can be used with linear scanning, compressive sensing, and interior tomography. A system of the subject invention can be tailored into permanent, movable, or reconfigurable systems as desired. Advanced image registration and spectral imaging features can be included as well.

Figure 1:
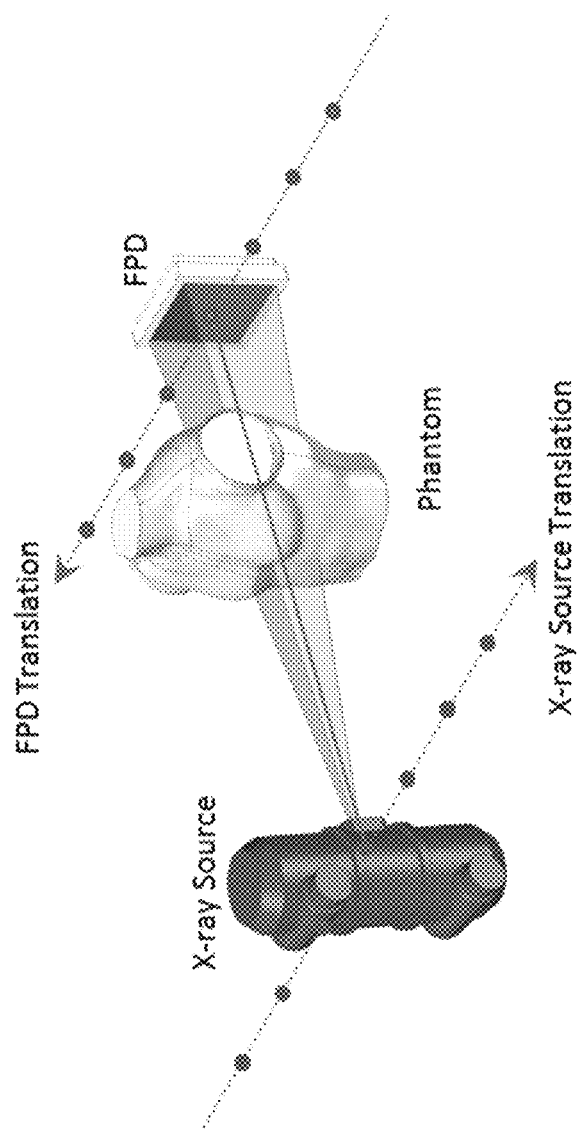
FIG. 1 shows a schematic of a system according to an embodiment of the subject invention.

FIG. 1 shows a schematic of a system according to an embodiment of the subject invention. Referring to FIG. 1, an energy source (e.g., an X-ray source) and a detector array (e.g., a linear array or a flat panel detector (FPD)) can be oppositely translated in parallel while a patient is fixed between them. That is, the source and the detector can be moved simultaneously in opposite or approximately opposite directions. The source and detector can be rotated such that they face each other as they are translated. Image reconstruction can be performed based on the results obtained by the detector. For example, 2-dimensional (2D) image reconstruction can be performed. Image reconstruction can be performed using, for example, fan beam geometry, though embodiments are not limited thereto.

In certain embodiments, an imaging method can use compressive sensing (CS)-based interior tomography techniques, and a data acquisition system can be made narrow to acquire a limited amount of truncated data. The source and detector can be translated oppositely (i.e., simultaneously in opposite or approximately opposite directions), such that different beam angles and ray paths with respect to the imaging object can be provided. Compared to related art parallel geometry, rotational movement can be substituted by one or more linear movements.

Various systems have been used to attempt to provide low-cost CT, including adapting real-time radiography (RTR) systems, using C-arms for cone-beam CT (CBCT), or extending earlier CT designs. However, no existing commercial medical CT scanner is available at an ultra-low cost (e.g., less than $150,000 (USD)). Certain scanning strategies are based on the rotation of an X-ray source and an associated X-ray detector array. The filtered back-projection-type algorithm requires a series of global projections over a full-scan or half-scan angular range. As a result, a gantry with a slip ring is indispensable, but this can be expensive and difficult to be moved around. The gantry rotation can be as fast as 4 turns per second, which is mainly for cardiac imaging applications. In many embodiments of the subject invention, a local X-ray CT scan is sufficient, and global reconstruction can be done by, e.g., performing a number of interior reconstructions. Certain embodiments of the subject invention can perform cardiac imaging tasks, while some embodiments are configured to not perform cardiac imaging tasks, since such tasks can sometimes require expensive equipment.

Interior tomography offers a theoretically exact solution to the long-standing "interior problem". In classic CT theory, an interior region of interest (ROI) cannot be exactly reconstructed only from truncated projections. Structures outside the ROI may disturb the features inside the ROI. The interior problem can be exactly and stably solved if a sub-region in the ROI is known, which is referred to as knowledge-based interior tomography. However, it is not easy to obtain precise prior knowledge of a sub-region in many cases. Compressive sensing (CS) allows an interior ROI to be exactly and stably reconstructed via minimizing its total variation (TV) or high order TV if the ROI is piecewise constant or polynomial, and this can be referred to as CS-based interior tomography.

Many embodiments of the subject invention include a translation-based CT scanning method, which can be similar to linear tomosynthesis scanning. Tomosynthesis, also known as digital tomosynthesis, is a method for performing high-resolution, limited-angle tomography. A linear tomosynthesis system can combine an X-ray tube and a flat panel detector (FPD) with tube/detector parallel translation. A small number of discrete projections can be used to reconstruct a series of slices at different depths at various thicknesses. An algorithm can be used, such as an iterative algorithm (e.g., expectation maximization).

Embodiments of the subject invention can provide ultra-low-cost and yet quality performance and can be instrumental in meeting medical imaging needs in developing countries, especially in rural areas. Linear scanning, fan-beam geometry, compressive sensing, and/or interior tomography, which can be easily extended to cone-beam geometry, can be used.

In an embodiment, a method of data acquisition can be based on linear or translational movement of an energy source (e.g., an X-ray source) and a detector array. FIG. 1 shows a schematic of a system according to an embodiment of the subject invention. Referring to FIG. 1, an energy source (e.g., an X-ray source) and a detector array (e.g., a linear array or a flat panel detector (FPD)) can be oppositely translated in parallel while a patient is fixed between them. Image reconstruction can be performed based on the results obtained by the detector. For example, 2-dimensional (2D) image reconstruction can be performed. Image reconstruction can be performed using, for example, fan beam geometry, though embodiments are not limited thereto. In an embodiment, the detector array can be considered as 1-dimensional (1D) with equally spaced bins.

Figure 2:
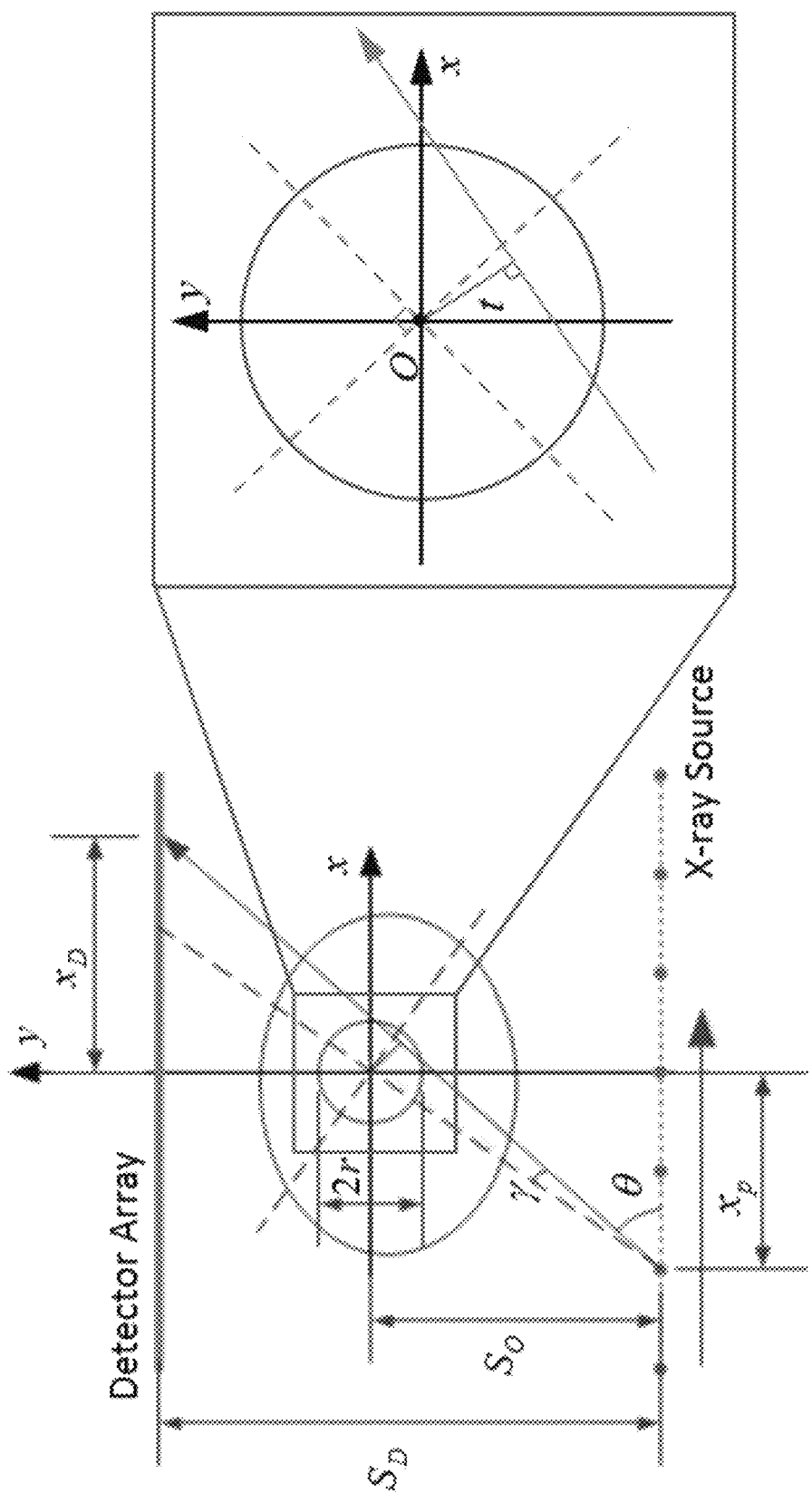
FIG. 2 shows a diagram demonstrating image geometry.

FIG. 2 shows a diagram demonstrating image geometry in a case where the detector array is long and there is no limit of the translational axis. Referring to FIG. 2, the xoy coordinate system can be fixed with respect to the patient, with the origin at the center of an ROI of radius r. Given a source position xp (p=1, . . . , P), where P is the number of projections acquired during the translation of the source, the ray reaching a detector cell through the center of the ROI can be referred to as the central ray of the projection with the central detector location $x_p$. An angle θ relative to the x-axis can specify a projection, and an angle γ can denote a ray within the fan beam geometry. $S_o$ is the distance from the source to the center of ROI along the y-axis, and $S_D$ is the distance from the energy source (e.g., X-ray source) to the detector along the y-axis. The translational movement of the source can be parallel to the x-axis, and the detector can also be aligned to be parallel to the x-axis. In a 2D plane, each single ray can also be defined by the two parameters t and θ. This can be described by the following two equations:

$$\theta = \tan^{-1}\left(\frac{S_D}{x_D - x_p}\right), \quad (1)$$

where $x_D$ is the distance from the center of the ROI to a detector cell along the x-axis. Let γ=arctan $$\left(\frac{S_D}{-x_p}\right) - \theta,$$

and the distance t from the center of the ROI to the ray (θ,γ) can be obtained:

$$t = (x_p^2 + S_o^2)^{\frac{1}{2}} \sin\gamma. \quad (2)$$

The parameter t in Equation (2) is in the interval [−r, r].

Figure 3A:
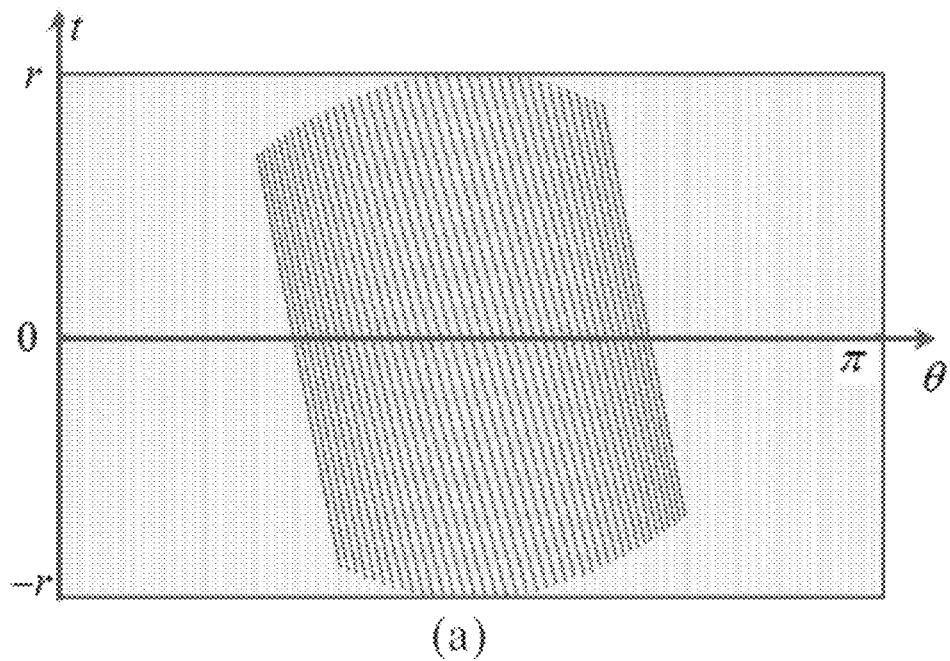
FIG. 3A shows a sample plot of data.
Figure 3B:
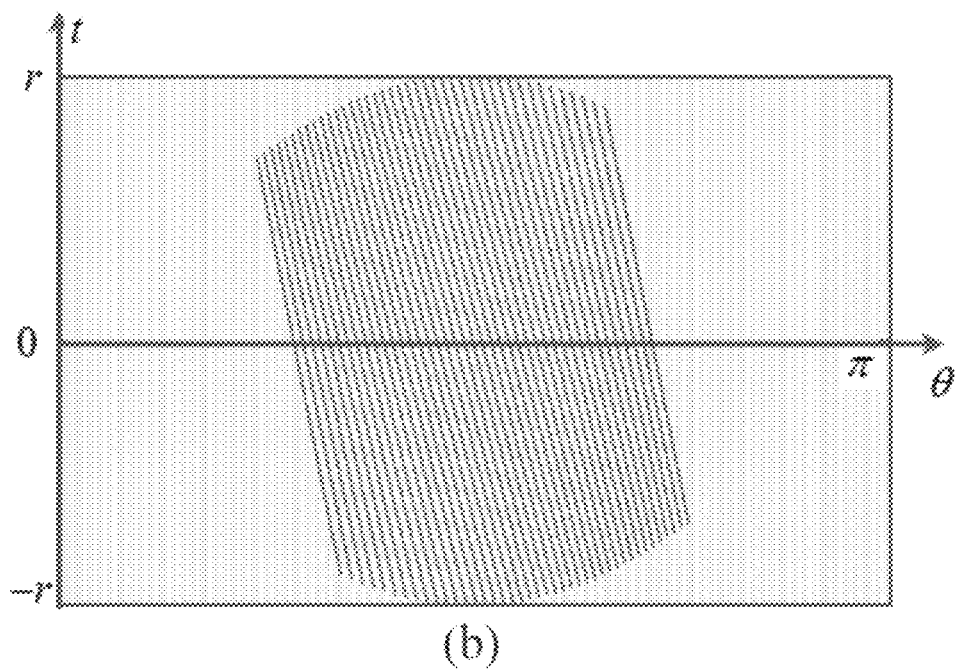
FIG. 3B shows a sample plot of data.

FIGS. 3A and 3B each shows a rectangular data region in the t−θ coordinate system partially filled by a single translation of the source. FIG. 3A shows sampled data from equi-spatial source positions, and FIG. 3B shows the counterpart from equi-angular source positions. To reconstruct an object exactly, the classic prerequisite is a complete dataset in the parallel beam geometry; i.e., the parallel projections should be available for a 180° angular range, as depicted in a rectangular area between θ=0 and θ=π in FIG. 3A. This requirement is satisfied by many CT acquisition geometries. However, the projections from a single translation (1T) of a data acquisition mode may only cover part of the rectangular area, as shown in FIG. 3A. This area can be determined using Equations (1) and (2) in the t−θ coordinate system. In FIG. 3A, each line depicts the data measured at one source position, and 41 source positions were equidistantly sampled between the tube start and end positions whose geometrical parameters are in Table 1. It can be useful to determine how much information can be obtained from a single translation compared to the standard 2D parallel-beam geometry.

TABLE 1

Geometrical parameters for the plots in FIG. 3

| Parameter | Value |
|---|---|
| Source to detector distance $S_D$ (mm) | 1000 |
| Source to object distance $S_o$ (mm) | 500 |
| Detector cell size (mm) | 1 |
| ROI diameter (mm) | 256 |
| Source translation distance $D_s$ (mm) | 800 |
| Source positions per translation P | 41 |

In certain cases, a single equal-spatial translation of the source may yield insufficient data and may also produce inhomogeneous data points in the sonogram, as shown in FIG. 3A. The source points for the single translation can be adjusted for better performance.

A variable can be defined, $\phi = \theta_{(t=0)}$, as the angle between the central ray and the x-axis to specify a source position. Then, the general sampling scheme can be as follows:

$$\varphi_0 = \tan^{-1}\left(\frac{S_o}{-x_0}\right) \quad (3)$$

$$\varphi_{P-1} = \tan^{-1}\left(\frac{S_o}{-x_{P-1}}\right)$$

$$\Delta\varphi = \frac{1}{P-1}(\varphi_{P-1} - \varphi_0)$$

$$x_p = S_o \cot(\varphi_0 + p\Delta\varphi)$$

where p=0, . . . , P−1, P is the number of source positions per translation, and Δφ is an angle between two projections in the t−θ coordinate system (i.e., the angle between two lines in FIG. 3B). Δφ can be directly calculated in terms of the translational endpoints of the source $x_0$ and $x_{P-1}$. As shown in FIG. 3B, the data coverage by a single translation can be significantly improved with the equal angular sampling, instead of equal spatial sampling.

Figure 4A:
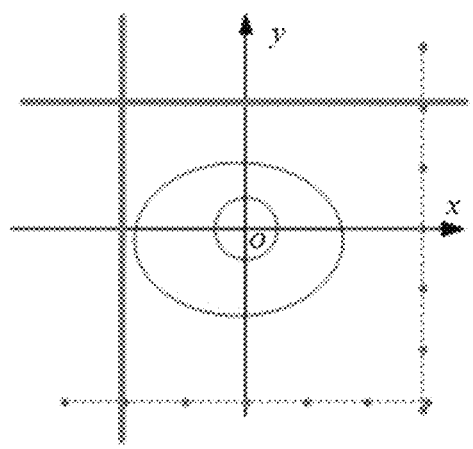
FIG. 4A shows a plot of a translation mode.
Figure 4B:
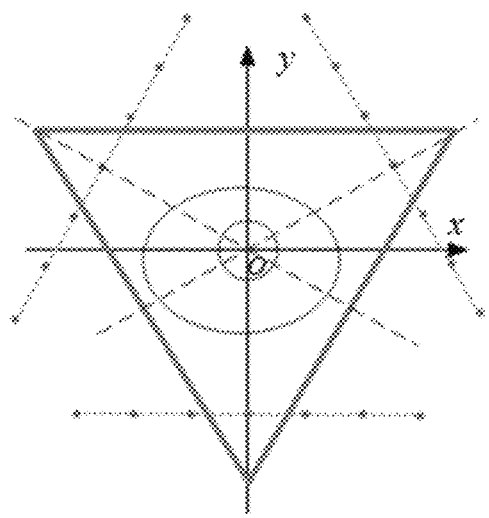
FIG. 4B shows a plot of a translation mode.
Figure 4C:
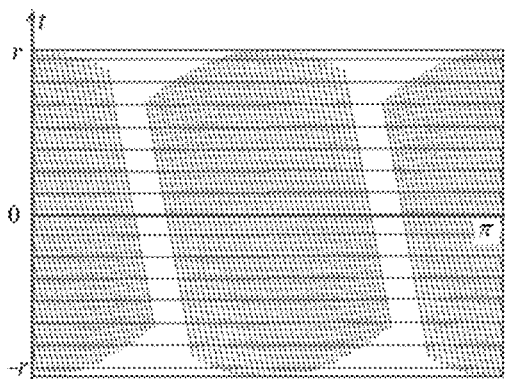
FIG. 4C shows a sample plot of data.
Figure 4D:
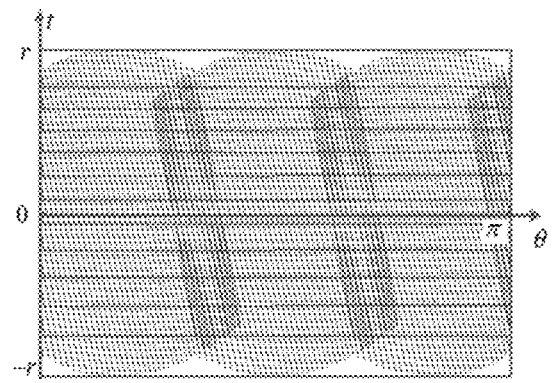
FIG. 4D shows a sample plot of data.
Figure 4E:
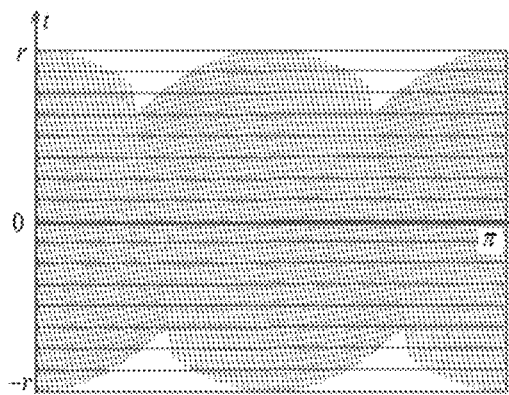
FIG. 4E shows a sample plot of data.
Figure 4F:
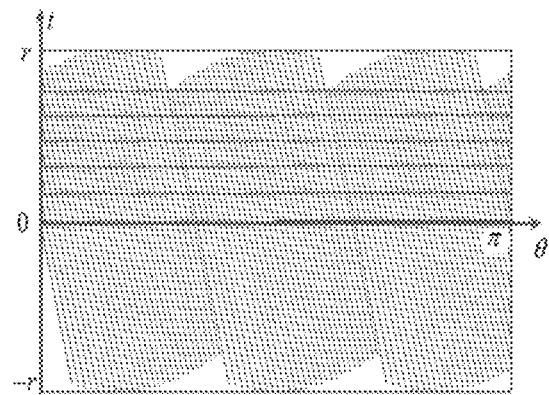
FIG. 4F shows a sample plot of data.

FIGS. 4A and 4B show plots of different translation modes using an equi-spatial source sampling scheme and an equi-angular sampling scheme. FIGS. 4C and 4D show rectangular data regions in the t−θ coordinate system for an equi-spatial source sampling scheme, and FIGS. 4E and 4F show rectangular data regions in the t−θ coordinate system for the an-angular source sampling scheme. FIGS. 4A, 4C, and 4E are for a mode using two translations (2T), such as two orthogonal translations. FIGS. 4B, 4D, and 4F are for a mode using three translations (3T), such as three symmetric translations. For the data obtained in FIG. 4, the source to detector distance was $S_D$=1000 mm, the source to object distance was $S_o$=500 mm, and the translation distances $D_S$ were 800 mm, 800 mm, 1000 mm, and 577 mm for FIGS. 4C, 4D, 4E, and 4F, respectively.

In order to cover a larger fraction of the full 180° angular range, the data acquisition scheme can be applied more than once. For example, two translations (2T) or three translations (3T) can be used. In certain embodiments, two orthogonal translations or three symmetric translations can be used. In each translation, the source can be linearly moved to acquire data. For example, referring to FIGS. 4A (2T scheme) and 4B (3T scheme), the source can be linearly moved to acquire data on red points, and the corresponding linear detector array is marked in green. Gaps may exist in 1T and 2T schemes, and overlaps may exist in a 3T scheme. Ideally, there would be neither gaps nor overlaps within the t−θ coordinate system. The translation distance $D_s$ can be optimized for the 2T and 3T schemes to cover the full data range better, as shown in FIGS. 4E and 4F.

In many embodiments, an imaging system can be modeled as a linear matrix equation in terms of the pixel basis:

$$AX=b, \quad (4)$$

where $b=(b^1, b^2, \ldots, b^M) \in R^M$ represents measured projection data with M being the total number of the data, $X = (X_1, \ldots, X_N) \in R^N$ denotes an object to be reconstructed with N being the total number of the pixels, and $A=(\alpha_{mn})$ is the system measurement matrix with m=1, . . . , M, n=1, . . . , N.

The algebraic reconstruction technique (ART) is an iterative algorithm used for CT reconstruction, and simultaneous ART (SART) is a refinement to the ART. Acceleration techniques for iterative reconstruction have been developed for SART, among which the ordered-subset (OS) scheme is very effective. The resultant algorithm can be called ordered-subset SART (OS-SART). Let the index set B={1, . . . , M} be partitioned into T nonempty disjoint subsets $B_t = \{i^t_1, \ldots, i^t_{M(t)}\}$, then $$B = \{1, \ldots, M\} = \bigcup_{0 \leq t \leq T-1} B_t \quad (5)$$

and the OS-SART formulation is as follows:

$$X_n^{(k+1)} = X_n^{(k)} + \sum_{m \in B_{[k \bmod T]}} \frac{a_{mn}}{a_{+n}} \frac{b_m - A^m X^{(k)}}{a_{m+}} \quad (6)$$

where $\alpha_{m+} \equiv \sum_{n=1}^{N} \alpha_{mn} \neq 0, \alpha_{+n} \equiv \sum_{m=1}^{M} \alpha_{mn} \neq 0$, and k is the iteration index.

The above OS-SART method can be combined with compressive sensing (CS) to improve the image quality in the case of sparse measurements. A well-known sparse transform is the discrete gradient transform (DGT). Hence, an ROI image can be reconstructed by minimizing the $l_1$-norm of its DGT, which can be referred to as the TV minimization and can be expressed as $$\min_X \|\nabla X\|_1, \text{ subject to } AX=b_s, X_n \geq 0, \quad (7)$$

where $\|\nabla X\|_1$ denotes TV of X, and $$\|\nabla X\|_1 = \sum_{i,j} d_{i,j}, \quad (8)$$

$$d_{i,j} = \sqrt{(X_{i,j} - X_{i+1,j})^2 + (X_{i,j} - X_{i,j+1})^2}$$

where $X_{i,j}$ is a pixel value of a discrete 2D image, and $d_{i,j}$ is the corresponding DGT. Because a 2D image can be easily rearranged into a 1D vector, both $X_{i,j}$ and $X_n$ can be used to represent the same image pixel.

Equation (7) can be solved in two loops. While an outer loop implements OS-SART to reduce data discrepancy, an inner loop can minimize the image TV. In the inner loop, a steepest gradient descent search can be used:

$$X_n^{(l+1)} = X_n^{(l)} - \lambda \omega \upsilon, \quad (9)$$

where $\lambda$ is a control parameter, $\upsilon = (\partial \|\nabla X\|_1 / \partial X_{i,j})|_{X_{i,j} = X_{i,j}[k,l]}$ is the gradient direction with respect to $X_{i,j} = X_{i,j}$ [k,l], $\omega = \max(X_n^{(l)})/\max(|\upsilon|)$ is a scaling constant, and k and l are the outer and inner loop indices. (The gradient direction with respect to $X_{i,j} = X_{i,j}$ [k,l] can also be $\upsilon = (\partial \|nabla X\|_1 / \partial X_{i,j})|_{X_{i,j} = X_{i,j}[k,l]}$.) The whole iterative procedure can be summarized as follows:
Step 1. Input data: b and let X=0;
Step 2. Calculate the current image using Equation (6);
Step 3. Minimize the TV of the current image X using Equation (9);
Step 4. Go to Step 2 until a stopping criterion is met.

In certain embodiments, an imaging system can include a computer-readable medium having computer-executable instructions for performing a CS-based interior tomography technique. For example, the instructions can be for performing the algorithm described above.

Figure 8A:
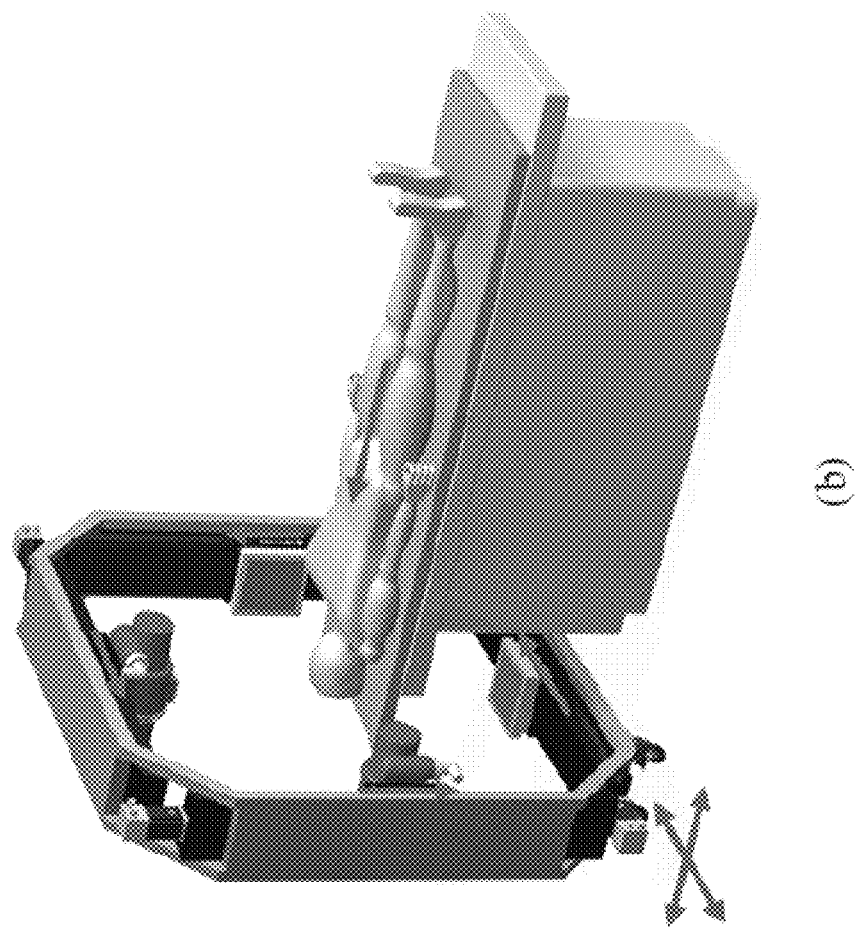
FIG. 8A shows a schematic of a system according to an embodiment of the subject invention.

FIG. 8A shows a schematic of a system according to an embodiment of the subject invention. Referring to FIG. 8A, in an embodiment, the system can be configured for a vertical patient position. A source-detector frame can be supported on a fixed central stage, and a patient can sit on a chair or stand against a vertical support, which can also be attached to the stage. The patient can be positioned in such a way that minimal motion would occur, e.g., using a padded seat with arm rests. The source and detector can be respectively mounted on two motorized linear stages, and can be translated oppositely (e.g., under personal computer (PC) control). The source-detector frame can be manually rotated around the central stage. The scanning position can be selected by adjusting the heights of the source and detector panels, aided by a laser beam. During a scan, the patient remains stationary. The source-detector frame can be oriented at 2 or 3 (or more) positions to realize the 2T or 3T (or four or more translation) modes. This proposed system can be useful when the patient is able to sit (e.g., for chest or head imaging) or stand (e.g., for abdominal imaging). However, it may not necessarily be suitable for all patients. The system can also be used in the 1T scanning mode for digital tomosynthesis or as a conventional radiographic device coupled with software.

Figure 8B:
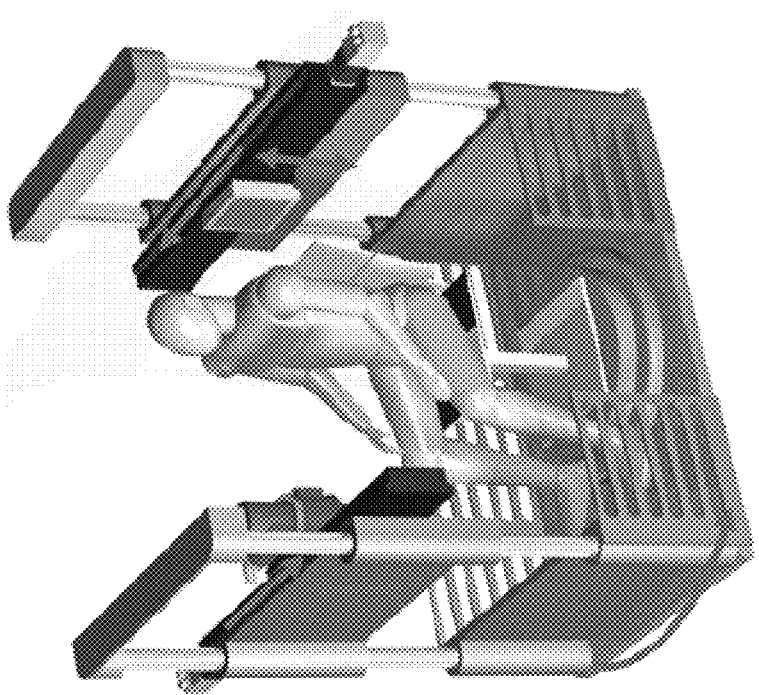
FIG. 8B shows a schematic of a system according to an embodiment of the subject invention.

FIG. 8B shows a schematic of a system according to an embodiment of the subject invention. Referring to FIG. 8B, in an embodiment, the system can be configured for a horizontal patient position. Two source-detector pairs can be used. A manually-adjustable patient bed can be used for patient translation, though embodiments are not limited thereto. In a particular embodiment, casters (e.g., four casters) can be fixed on the frame. With two laser beams, the scan position can be selected, and the casters (if present) can be locked. The sources and detectors can be respectively mounted on four motorized linear stages for the 2T scanning mode. The two source-detector pairs can be translated simultaneously. This proposed system can be used as a conventional CT scanner with a 10-second scan time. It is consistent with a single patient breath hold, and with a reasonable acceleration and deceleration time to minimize patient discomfort. Thus, it would be suitable for almost all patients.

Systems of the subject invention can advantageously be very cost-effective. While related art low-end CT systems still have a cost in a range of $300,000 (US dollars) $600,000 (US dollars), systems of the subject invention can be significantly cheaper. For example, systems of the subject invention can have a total cost of less than $150,000, less than $125,000, less than $100,000, less than $75,000, or even less than $54,000 (all values are in US dollars). Systems of the subject invention can include <1 mm spatial resolution, 2 kVp settings, 3-second linear translation, and noise and dose indices comparable to those of related art systems. With these values, estimated system costs are listed in Table 2, with "vertical system" referring to a system as shown in FIG. 8A and "horizontal system" referring to a system as shown in FIG. 8B.

TABLE 2

Cost estimates of the proposed low-end CT scanners

| | | | Vertical system | | | Horizontal system | | |
|---|---|---|---|---|---|---|---|---|
| No. | Subsystem | Supplier | Unit price | Quantity | Cost | Unit price | Quantity | Cost |
| 1 | X-ray Source | Toshiba | $5,000 | 1 | $5,000 | $5,000 | 2 | $10,000 |
| 2 | Flat Panel Detector | Samsung/ PerkinElmer | $30,000 | 1 | $30,000 | $30,000 | 2 | $60,000 |
| 3 | Mechanical control | From China | $15,000 | 1 | $15,000 | $22,000 | 1 | $22,000 |
| 4 | Computer | | $1,500 | 1 | $1,500 | $1,500 | 1 | $1,500 |
| 5 | Software | | $2,000 | 1 | $2,000 | $2,000 | 1 | $2,000 |
| | Total cost | | | | $53,500 | | | $95,500 |

Embodiments of the subject invention include imaging an ROI by translating an energy source (e.g., an X-ray source) and detector pair. Different translational modes (e.g., 1T, 2T, 3T, four or more) can be used. While the 1T mode may give low image quality, the optimized 2T and 3T modes yield excellent imaging performance as discussed in Examples 1 and 2. A simplest searching method can be used to minimize the TV, though embodiments are not limited thereto. More complicated methods can be used as well, such the soft-threshold filtering method. If the source sampling is dense enough, a filtered back-projection algorithm can be applicable in 2T and 3T modes.

In order to deliver adequate image quality, motion artifacts that may occur during scanning should be handled, especially for a vertical architecture (see, e.g., FIG. 8A). Although the patient can be asked to stay still during a scan, respiratory and other physiological movements are often unavoidable. Thus, reconstructed image quality may not be as high as a state-of-the-art scanner in some cases. However, computational methods can be used to correct motion artifacts effectively. For example, such methods can be based on motion models or data consistency. Low-cost systems of the subject invention can use high-tech computational methods in order to deliver optimized imaging outcomes to a patient.

In addition to interior reconstruction, methods and systems of the subject invention also allow digital tomosynthesis and interior and global scans (e.g., aided by advanced software). For example, a global scan can be achieved by combining multiple interior scans. A more optimized global scanning mode can be to translate a detector array for each fixed source position. Multiple scanning protocols can also be used.

While modern CT scanners are popular in the developed countries, there is an urgent demand for low-end CT systems in developing countries, especially in rural areas. Embodiments of the subject invention advantageously address this demand by providing translation-based data acquisition methods and a corresponding reconstruction algorithm or algorithms. Excellent image quality can be achieved, and a detailed cost analysis shows that the overall system cost can be below $100,000 (US dollars) or even less than $54,000 (US dollars).

The methods and processes described herein can be embodied as code and/or data. The software code and data described herein can be stored on one or more computer-readable media, which may include any device or medium that can store code and/or data for use by a computer system. When a computer system reads and executes the code and/or data stored on a computer-readable medium, the computer system performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that is capable of storing computer-readable information/data. Computer-readable media should not be construed or interpreted to include any propagating signals.

A greater understanding of the present invention and of its many advantages may be had from the following examples, given by way of illustration. The following examples are illustrative of some of the methods, applications, embodiments and variants of the present invention. They are, of course, not to be considered as limiting the invention. Numerous changes and modifications can be made with respect to the invention.

Example 1

Figure 5:
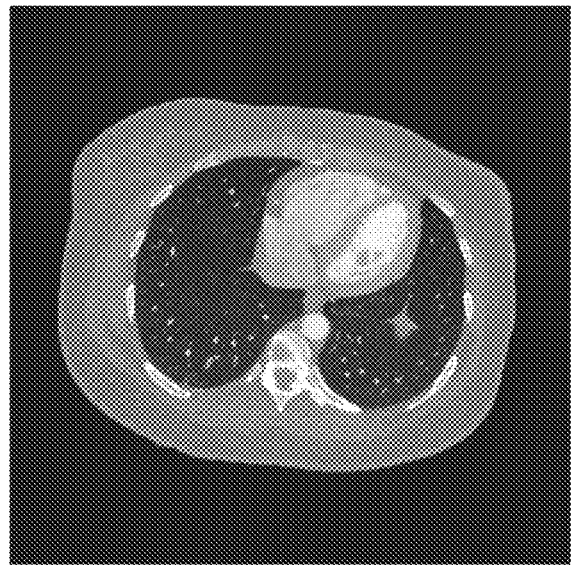
FIG. 5 shows a numerical cardiac phantom.
Figure 6A:
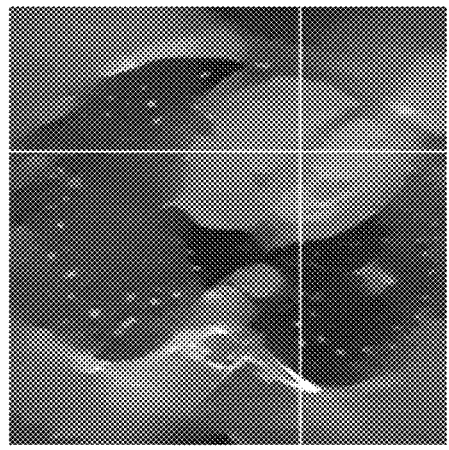
FIG. 6A shows an image obtained by a noise-free projection in single translation.
Figure 6B:
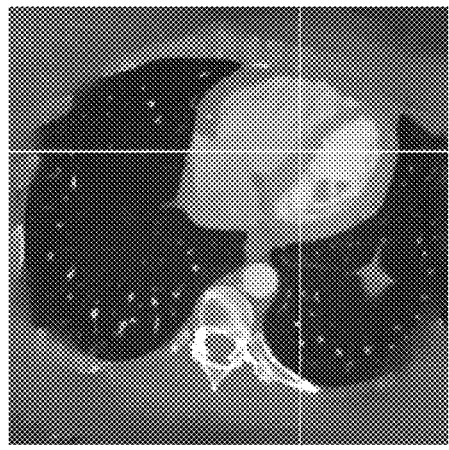
FIG. 6B shows an image obtained by a noise-free projection with two translations.
Figure 6C:
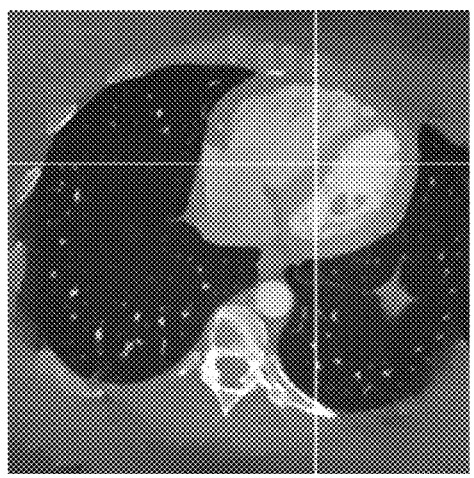
FIG. 6C shows an image obtained by a noise-free projection with three translations.
Figure 6D:
FIG. 6D shows an image of a phantom.

A data acquisition method of the subject invention was evaluated using a numerical simulation. A reconstruction program was implemented in MatLab for interior reconstruction in fan-beam geometry. FIG. 5 shows the numerical cardiac phantom that was used for realistic simulation (in a display window of [−1000, 1000] HU). The phantom had 700×700 pixels, each of which covered an area of 0.5 mm×0.5 mm resulting in a rectangular compact support of 350 mm×350 mm. Other imaging parameters for 1T, 2T, and 3T are shown in Table 3. The pixel size of the reconstructed image was set to 0.7 mm×0.7 mm. In the OS-SART algorithm, the subset number was set to 6, and each subset took 40 views for each of the data acquisition modes. The pseudo-code for the TV minimization can be found. The initial value of $\lambda$ was set to 0.005 and attenuated with a constant factor 0.995 after each iteration. The stopping criterion was to reach a maximum number of iterations.

FIG. 6 shows magnified 300×300 cardiac regions in the reconstructed images after 120 iterations (in a display window of [−1000, 1000] HU). FIG. 6A shows an image obtained by a noise-free projection in single translation, FIG. 6B shows an image obtained by a noise-free projection with two translations, FIG. 6C shows an image obtained by a noise-free projection with three translations, and FIG. 6D shows the original phantom as a reference.

Figures 7A, 7B:
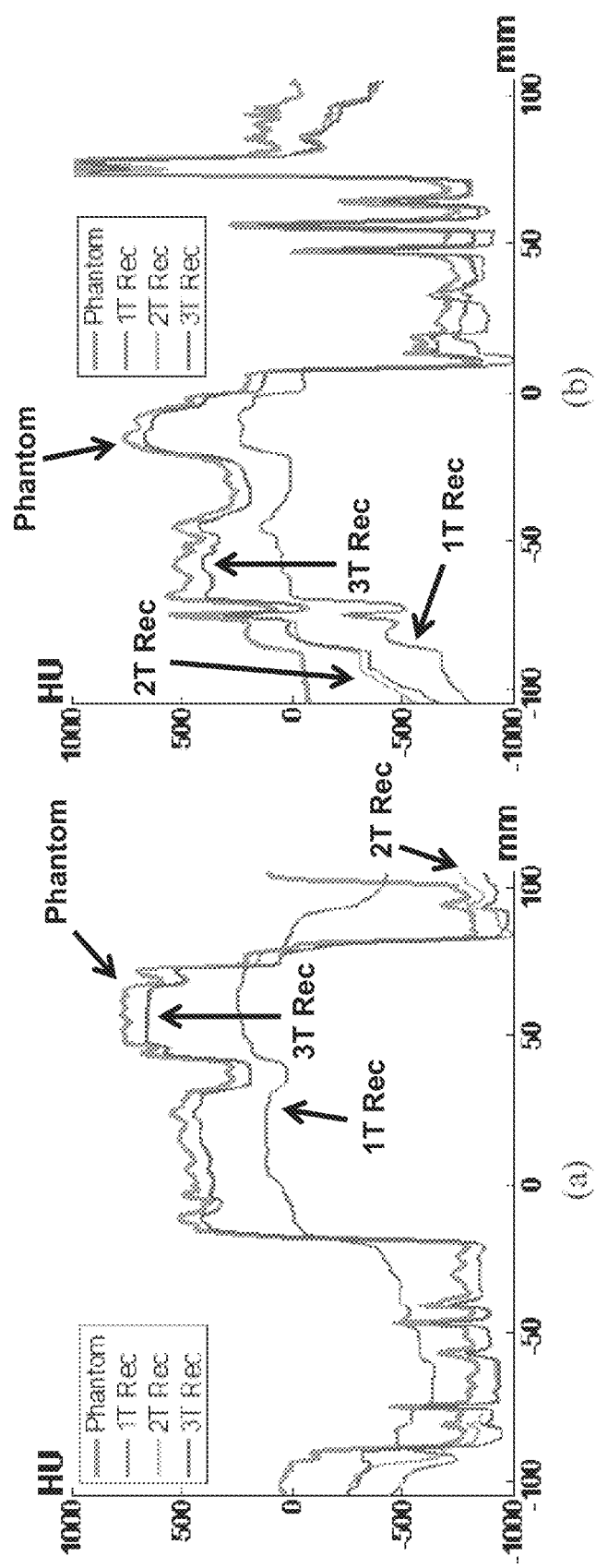
FIG. 7A shows a plot of a representative profile along the horizontal line of FIGS. 6A-6D.
FIG. 7B shows a plot of a representative profile along the vertical line of FIGS. 6A-6D.

It can be seen that the image quality associated with 1T is inferior to that with either 2T or 3T. This is because the data acquired from 1T cannot sufficiently cover the full data range, involving truncated and limited data issues. FIGS. 7A and 7B show representative profiles along the horizontal (FIG. 7A) and vertical (FIG. 7B) white lines in FIGS. 6A-6D. Some differences exist between the profiles of the original phantom and reconstructed images. This may be due to three reasons. First, interior tomography is formulated in the continuous domain which requires infinitely many views; however, only employed 240 views were employed. Second, the iterative algorithm will converge to the true solution only after infinite iterations, while the iteration was stopped after 120 iterations in this simulation. Third, the image phantom is from a clinical application, which does not rigidly satisfy the piecewise constant image model.

TABLE 3

Parameters for the numerical simulation

| Parameter | Value |
| --- | --- |
| Source to detector distance $S_D$ (mm) | 1200 |
| Source to object distance $S_o$ (mm) | 600 |
| Detector mode | equi-spatial |
| Detector array length (Pixel) | 400 |
| Detector pixel size (mm) | 1.0 |
| ROI diameter (mm) | 166 |
| Number of source points per translation P (1T) | 240 |
| Number of source points per translation P (2T) | 120 |
| Number of source points per translation P (3T) | 80 |
| 1T translation distance | 1200 |
| 2T translation distance | 1200 |
| 3T transtation distance | 693 |

TABLE 3-continued

Parameters for the numerical simulation

| Parameter | Value |
|---|---|
| Translation mode | equi-angular |
| Reconstruction matrix | 500 × 500 |
| Pixel size (mm 2) | 0.7 × 0.7 |

Example 2

Figures 9A, 9B:
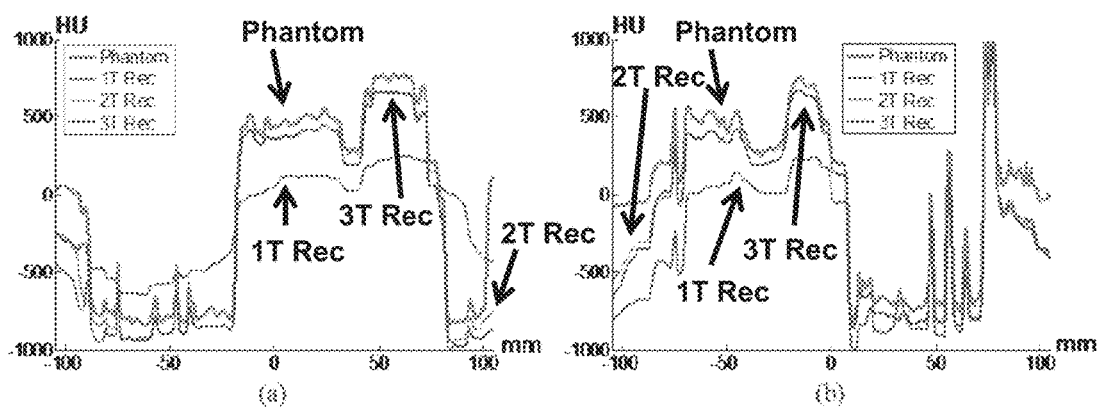
FIG. 9A shows a reconstruction of FIG. 7A, reconstructed from noisy projections.
FIG. 9B shows a reconstruction of FIG. 7B, reconstructed from noisy projections.
Figure 10A:
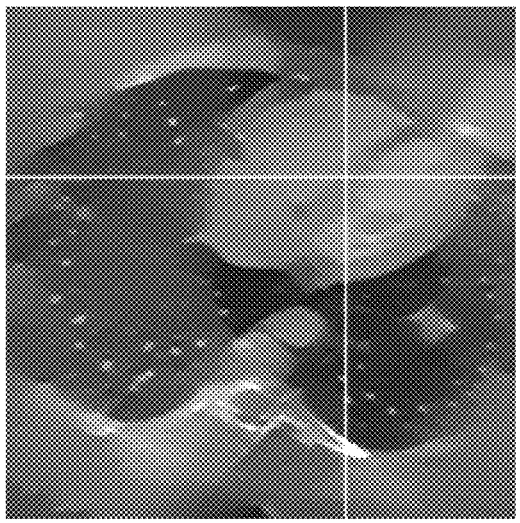
FIG. 10A shows a reconstruction of FIG. 6A, reconstructed from noisy projections.
Figure 10B:
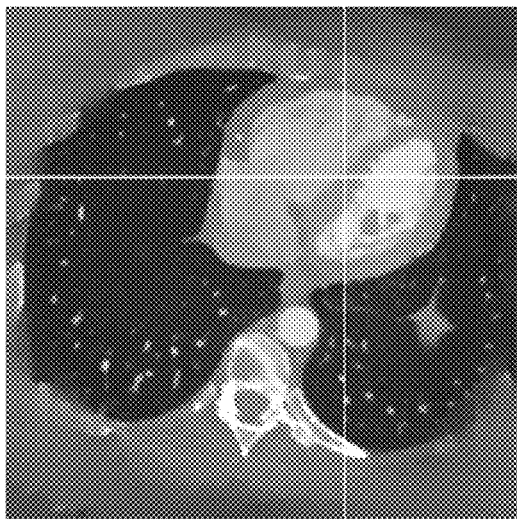
FIG. 10B shows a reconstruction of FIG. 6B, reconstructed from noisy projections.
Figure 10C:
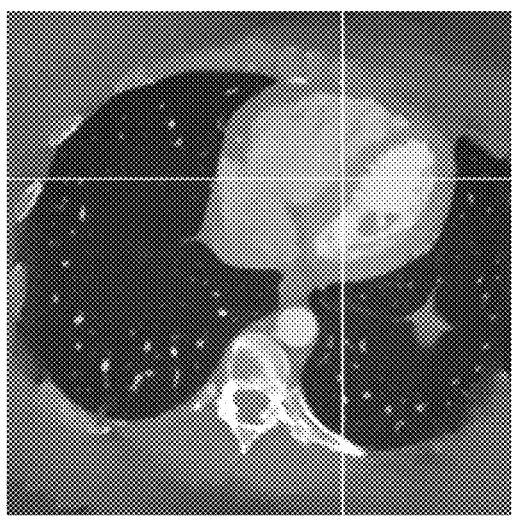
FIG. 10C shows a reconstruction of FIG. 6C, reconstructed from noisy projections.
Figure 10D:
FIG. 10D shows a reconstruction of FIG. 6D, reconstructed from noisy projections.

In practical applications, measurement noise is unavoidable. To test the stability of the a data acquisition method of the subject invention and the associated algorithms against data noise, the tests of Example 1 were repeated using projections corrupted by Poisson noise, assuming 5×10⁴ photons per detector element. The results are shown in FIGS. 9 and 10. FIGS. 9A and 9B show reconstructions of FIGS. 7A and 7B, respectively, reconstructed from noisy projections. FIGS. 10A-10D show reconstructions of FIGS. 6A-6D, respectively, reconstructed from noisy projections. The results show a satisfactory stability of the imaging performance.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein (including those in the "References" section) are incorporated by reference in their entirety, including all figures and tables, to the extent they are not inconsistent with the explicit teachings of this specification.

REFERENCES

ANDERSEN, A. et al., "Simultaneous algebraic reconstruction technique (SART) A superior implementation of the art algorithm," *Ultrasonic Imaging*, 1984, 6(1):81-94.

BREHM, M. et al., "Artifact-resistant motion estimation with a patient-specific artifact model for motion-compensated conebeam CT," *Medical Physics*, 2013, 40(10).

CANDES, E., et al., "Robust uncertainty principles: Exact signal reconstruction from highly incomplete frequency information," IEEE *Transactions on Information Theory*, 2006, 52(2):489-509.

CHEN, G. H. et al., "Prior image constrained compressed sensing (PICCS): A method to accurately reconstruct dynamic CT images from highly undersampled projection data sets," *Medical Physics*, 2008, 35(2):660-663.

COURDURIER, M. et al., "Solving the interior problem of computed tomography using a priori knowledge," *Inverse Problems*, 2008, 24(6).

DOBBINS, J. T., III, et al., "Initial investigation into lower-cost CT for resource limited regions of the world, in Medical Imaging 2010: Physics of Medical Imaging," E. Samei and N. J. Pelc, Editors. 2010.

DONOHO, D., "Compressed sensing," *IEEE Transactions on Information Theory*, 2006. 52(4):1289-1306.

FELDKAMP, L., et al., "Practical cone-beam algorithm," *Journal of the Optical Society of America a-Optics Image Science and Vision*, 1984, 1(6):612-619.

FLOHR, T. G. et al., "First performance evaluation of a dual-source CT (DSCT) system," *Eur Radiol*, 2006, 16(2):256-268.

FUCHS, V. R. et al., "Physicians' views of the relative importance of thirty medical innovations," *Health Aff*, 2001, 20(5):30-42.

GAO, H. et al., "Straight-line-trajectory-based x-ray tomographic imaging for security inspections: System Design, Image Reconstruction and Preliminary Results," *IEEE Transactions on Nuclear Science*, 2013, 3955-3968.

GORDON, R., et al., "Algebraic reconstruction techniques (ART) for 3-dimensional electron microscopy and X-ray photography," *Journal of Theoretical Biology*, 1970, 29(3):471&.

HUGHES, S. H. C. S. et al., "Development of a low cost computed tomography image processing system," in: *Applications of Optical Engineering: Proceedings of OE/Midwest '90*. 1991. Rosemont, Ill., USA: Publ by Int Soc for Optical Engineering, Bellingham, Wash., United States.

JENSEN, N. K. G. et al., "Prediction and reduction of motion artifacts in free-breathing dynamic contrast enhanced CT perfusion imaging of primary and metastatic intrahepatic tumors," *Academic Radiology*, 2013, 20(4): 414-422.

JIANG, M. et al., "Convergence studies on iterative algorithms for image reconstruction," *IEEE Trans Med Imaging*, 2003, 22:569-579.

KUDO, H. et al., "Tiny a priori knowledge solves the interior problem in computed tomography," *Phys Med Biol*, 2008, 53(9):2207-2231.

NATTERER, F. "The Mathematics of Computerized Tomography," *Classics in Applied Mathematics*, SIAM: Society for Industrial and Applied Mathematics, 2001.

RYBICKI, F. J. et al., "Initial evaluation of coronary images from 320-detector row computed tomography," *Int J Cardiovasc Imaging*, 2008, 24(5):535-546.

SCHON, T. et al., "A translation-based data acquisition method for computed tomography: Theoretical analysis and simulation study," *Medical Physics*, 2013, 40(8).

SECHOPOULOS, I. "A review of breast tomosynthesis. Part I. The image acquisition process," *Medical Physics*, 2013, 40(1).

SECHOPOULOS, I. "A review of breast tomosynthesis. Part II. Image reconstruction, processing and analysis, and advanced applications," *Medical Physics*, 2013, 40(1).

TONNA, J. E. et al., "Potentially low cost solution to extend use of early generation computed tomography," *The Western Journal of Emergency Medicine*, 2010, 11(5): 463-469.

VU, H. V., et al., "Local ROI Reconstruction via Generalized FBP and BPF Algorithms along more Flexible Curves," *International Journal of Biomedical Imaging*, 2006, 2006(2):Article ID:14989, 7 pages.

WANG, G. et al., "The meaning of interior tomography," *Physics in Medicine and Biology*, 2013, 58(16):R161-R186.

WANG, G. et al., "Ordered-subset simultaneous algebraic reconstruction techniques (OS-SART)," *Journal of X-Ray Science and Technology*, 2004, 12(3):169-177.

XU, Q. et al., "Statistical Interior Tomography," *IEEE Transactions on Medical Imaging*, 2011, 30(5):1116-1128.

YAMATO, R., et al., "Study of new linear movement tomography using magnification ratio," *Journal of Meikai University School of Dentistry*, 2005, 39-49.

YANG, J. S. et al., "High-order total variation minimization for interior tomography," *Inverse Problems*, 2010, 26(3): 29.

YE, Y., et al., "A general local reconstruction approach based on a truncated Hilbert transform," *International Journal of Biomedical Imaging*, 2007, 1-8, Article ID: 63634.

YU, H. et al., "A soft-threshold filtering approach for reconstruction from a limited number of projections," *Physics in Medicine and Biology*, 2010, 53(13):3905-3916.

YU, H. Y., et al., "Local ROI reconstruction via generalized FBP and BPF algorithms along more flexible curves," *International Journal of Biomedical Imaging*, 2006, 2006:2, Article ID: 14989, p. 7.

YU, H. et al., "Compressed sensing based Interior tomography," *Phys Med Biol*, 2009, 54(9):2791-2805.

What is claimed is:

1. An imaging method, comprising:
    positioning an X-ray source on a first side of a subject to be imaged such that the X-ray source faces the subject;
    positioning a detector on a second side of the subject such that the detector faces the subject;
    linearly translating the X-ray source and the detector by simultaneously moving the X-ray source and the detector in opposite or approximately opposite directions while the X-ray source supplies X-rays and the detector acquires tomographic data of the subject; and
    reconstructing a Computed Tomography (CT) image based on the tomographic data
    wherein linearly translating the X-ray source and the detector is performed twice, and
    wherein a first path traveled by the X-ray source during the first linear translation step is orthogonal to a second path traveled b the X-ray source during the second linear translation step.

2. The imaging method according to claim 1, wherein the subject is a human patient.

3. The imaging method according to claim 1, wherein an entire length of the first path traveled by the X-ray source during the first linear translation step is equal to an entire length of the second path traveled by the X-ray source during the second linear translation step and an entire length of a third path traveled by the X-ray source during a third linear translation step.

4. The imaging method according to claim 1, wherein reconstructing a CT image based on the tomographic data comprises:
    modeling the acquired data as a linear matrix equation (b) based on a pixel basis;
    modeling the CT image to be reconstructed as a linear matrix equation (X) based on a pixel basis; and
    performing the following algorithm:
        step 1—input data: b and let X=0;
        step 2—calculate the current image;
        step 3—minimize the total variation (TV) of the current image X; and
        step 4—go to step 2 until a stopping criterion is met.

5. An imaging method, comprising:
    positioning an X-ray source on a first side of a subject to be imaged such that the X-ray source faces the subject;
    positioning a detector on a second side of the subject such that the detector faces the subject;
    linearly translating the X-ray source and the detector by simultaneously moving the X-ray source and the detector in opposite or approximately opposite directions while the X-ray source supplies X-rays and the detector acquires tomographic data of the subject; and
    reconstructing a Computed Tomography (CT) image based on the tomographic data,
    wherein reconstructing a CT image based on the tomographic data comprises:
    modeling the acquired data as a linear matrix equation (b) based on a pixel basis;
    modeling the CT image to be reconstructed as a linear matrix equation (X) based on a pixel basis; and
    performing the following algorithm:
        step 1—input data: b and let X=0
        step 2—calculate the current image;
        step 3—minimize the total variation (TV) of the current image X; and
        step 4—no to step 2 until a stopping criterion is met,
    wherein step 2—calculate the current image comprises calculating the image using the following equation:

$$X_n^{(k+1)} = X_n^{(k)} + \sum_{m \in B_{[k \bmod T]}} \frac{a_{mn}}{a_{+n}} \frac{b_m - A^m X^{(k)}}{a_{m+}}$$

where $\alpha_{m+} \equiv \sum_{n=1}^{N} \alpha_{mn} \neq \alpha_{+n} \equiv \sum_{m=1}^{M} \alpha_{mn} \neq 0$, and k is the iteration number
    where $A=(\alpha_{mn})$ is a system measurement matrix with $m=1, \ldots, M$ and $n=1, \ldots, N$, where an index set is partitioned into T nonempty disjoint subsets $B_t = \{i^t_1, \ldots, i^t_{M(t)}\}$, and where $$B = \{1, \ldots, M\} = \bigcup_{0 \leq t \leq T-1} B_t.$$

6. The imaging method according to claim 5, wherein step 3—minimizing the TV of the current image X comprises minimizing the TV of the current image X using the following formula:

$$X_n^{(l+1)} = X_n^{(l)} - \lambda \omega \upsilon,$$

where $\lambda$ is a control parameter, $\upsilon = (\partial \|\nabla X\|_1 / \partial X_{i,j})|_{X_{i,j}=X_{i,j}[k,l]}$ is the gradient direction with respect to $X_{i,j} = X_{i,j}[k,l]$, $\omega = \max(X_n^{(l)})/\max(|\upsilon|)$ is a scaling constant, and k and l are the outer and inner loop indices.

7. The imaging method according to claim 6, wherein the stopping criterion of step 4 is reaching a maximum number of iterations.

8. The imaging method according to claim 6, wherein linearly translating the X-ray source and the detector is performed twice, and
    wherein a first path traveled by the X-ray source during the first linear translation step is orthogonal to a second path traveled by the X-ray source during the second linear translation step.

9. The imaging method according to claim 6, wherein linearly translating the X-ray source and the detector is performed three times, and
    wherein an entire length of a first path traveled by the X-ray source during the first linear translation step is equal to an entire length of a second path traveled by the X-ray source during the second linear translation step and an entire length of a third path traveled by the X-ray source during the third linear translation step.

10. The imaging method according to claim 5, wherein the subject is a human patient.

11. The imaging method according to claim 5, wherein linearly translating the X-ray source and the detector is performed twice.

12. The imaging method according to claim 11, wherein a first path traveled by the X-ray source during the first linear translation step is orthogonal to a second path traveled by the X-ray source during the second linear translation step.

13. The imaging method according to claim 5, wherein linearly translating the X-ray source and the detector is performed three times.

14. The imaging method according to claim 5, wherein an entire length of a first path traveled by the X-ray source during a first linear translation step is equal to an entire length of a second path traveled by the X-ray source during a second linear translation step and an entire length of a third path traveled by the X-ray source during a third linear translation step.

15. An imaging system, comprising:
a main stage for a subject to be imaged;
a first X-ray source positioned to face the subject being imaged and configured to linearly translate while providing X-rays;
a first detector positioned to face the subject being imaged and to face the first X-ray source, and configured to linearly translate while acquiring tomographic data of the subject being imaged;
a frame comprising a first motorized linear stage and a second motorized linear stage;
a second X-ray source positioned to face the subject being imaged and configured to linearly translate while providing X-rays; and
a second detector positioned to face the subject being imaged and to face the second X-ray source, and configured to linearly translate while acquiring tomographic data of the subject being imaged,
wherein the imaging system is configured such that the first X-ray source and the first detector simultaneously move in opposite or approximately opposite directions while the first X-ray source supplies X-rays and the first detector acquires tomographic data,
wherein the first X-ray source is mounted on the first motorized linear stage,
wherein the first detector is mounted on the second motorized linear stage,
wherein the first motorized linear stage is configured to move the first X-ray source linearly,
wherein the second motorized linear stage is configured to move the first detector linearly in a direction that is opposite or approximately opposite to the direction in which the first X-ray source is moving,
wherein the imaging system is configured such that the second X-ray source and the second detector simultaneously move in opposite or approximately opposite directions while the second X-ray source supplies X-rays and the second detector acquires tomographic data,
wherein the frame further comprises a third motorized linear stage and a fourth motorized linear stage,
wherein the second X-ray source is mounted on the third motorized linear stage,
wherein the second detector is mounted on the fourth motorized linear stage,
wherein the third motorized linear stage is configured to move the second X-ray source linearly,
wherein the fourth motorized linear stage is configured to move the second detector linearly in a direction that is opposite or approximately opposite to the direction in which the second X-ray source is moving, and
wherein the main stage is configured to allow the subject to lie down while being imaged.

16. The imaging system according to claim 15, wherein the main stage is further configured to also allow the subject to stand up or sit down while being imaged.

17. The imaging system according to claim 15, wherein the first detector is a linear array or a flat panel detector (FPD).

18. The imaging system according to claim 15, further comprising a non-transitory computer-readable medium having computer-executable instructions that, when executed by a processor, performing a method comprising:
modeling acquired data as a linear matrix equation (b) based on a pixel basis;
modeling a CT image to be reconstructed as a linear matrix equation (X) based on a pixel basis; and
performing the following algorithm:
step 1—input data: b and let X=0;
step 2—calculate the current image;
step 3—minimize the total variation (TV) of the current image X; and
step 4—go to step 2 until a stopping criterion is met,
wherein step 2—calculate the current image comprises calculating the image using the following equation:

$$X_n^{(k+1)} = X_n^{(k)} + \sum_{m \in B_{[k \bmod T]}} \frac{a_{mn}}{a_{+n}} \frac{b_m - A^m X^{(k)}}{a_{m+}}$$

where $\alpha_{m+} \equiv \Sigma_{n=1}^{N} \alpha_{mn} \neq 0$, $\alpha_{+n} \equiv \Sigma_{m=1}^{M} \alpha_{mn} \neq 0$, and k is the iteration number,
where $A=(\alpha_{mn})$ is a system measurement matrix with m=1, . . . , M and n=1, . . . , N, where an index set is partitioned into T nonempty disjoint subsets $B_t = \{i^t_1, \ldots, i^t_{M(t)}\}$, and where $$B = \{1, \ldots, M\} = \bigcup_{0 \leq t \leq T-1} B_t,$$

and
wherein step 3—minimizing the TV of the current image X comprises minimizing the TV of the current image X using the following formula:

$$X_n^{(l+1)} = X_n^{(l)} - \lambda \omega \upsilon,$$

where $\lambda$ is a control parameter, $\upsilon = (\partial \|\nabla X\|_1 / \partial X_{i,j})|_{X_{i,j}=X_{i,j}[k,l]}$ is the gradient direction with respect to $X_{i,j}=X_{i,j}[k,l]$, $\omega = \max(X_n^{(l)})/\max(|\upsilon|)$ is a scaling constant, and k and l are the outer and inner loop indices.

19. The imaging system according to claim 15, wherein each of the first detector and the second detector is a linear array or an FPD.

20. The imaging system according to claim 19, further comprising a non-transitory computer-readable medium having computer-executable instructions that, when executed by a processor, perform a method comprising:
modeling acquired data as a linear matrix equation (b) based on a pixel basis;
modeling a CT image to be reconstructed as a linear matrix equation (X) based on a pixel basis; and
performing the following algorithm:
step 1—input data: b and let X=0;
step 2—calculate the current image;
step 3—minimize the total variation (TV) of the current image X; and
step 4—go to step 2 until a stopping criterion is met, wherein step 2—calculate the current image comprises calculating the image using the following equation:

$$X_n^{(k+1)} = X_n^{(k)} + \sum_{m \in B_{[k \bmod T]}} \frac{a_{mn}}{a_{+n}} \frac{b_m - A^m X^{(k)}}{a_{m+}}$$

where $\alpha_{m+} \equiv \sum_{n=1}^{N} \alpha_{mn} \neq 0, \alpha_{+n} \equiv \sum_{m=1}^{M} \alpha_{mn} \neq 0$, and k is the iteration number, where $A=(\alpha_{mn})$ is a system measurement matrix with m=1, ..., M and n=1, ..., N, where an index set is partitioned into T nonempty disjoint subsets $B_t = \{i^t_1, \ldots, i^t_{M(t)}\}$, and where $$B = \{1, \ldots, M\} = \bigcup_{0 \leq t \leq T-1} B_t,$$

and wherein step 3—minimizing the TV of the current image X comprises minimizing the TV of the current image X using the following formula:

$$X_n^{(l+1)} = X_n^{(l)} - \lambda \omega \upsilon,$$

where $\lambda$ is a control parameter, $\upsilon = (\partial \|\nabla X\|_1 / \partial X_{i,j})|_{Xi,j=Xi,j[k,l]}$ is the gradient direction with respect to $X_{i,j} = X_{i,j}[k,l]$, $\omega = \max(X_n^{(l)})/\max(|\upsilon|)$ is a scaling constant, and k and l are the outer and inner loop indices.

* * * * *